United States Patent [19]

Terman

[11] Patent Number: 5,533,527
[45] Date of Patent: Jul. 9, 1996

[54] TREATMENT METHOD FOR DEPRESSIVE AND NEUROVEGETATIVE DISORDERS

[75] Inventor: Michael Terman, New York, N.Y.

[73] Assignee: Columbia University, New York, N.Y.

[21] Appl. No.: 230,127

[22] Filed: Apr. 20, 1994

[51] Int. Cl.$^6$ ............................................. A61M 21/00
[52] U.S. Cl. ............................................. 128/898
[58] Field of Search ........................... 128/898; 607/45, 607/2; 600/27, 26; 361/231, 232

[56] References Cited

U.S. PATENT DOCUMENTS

| | | | |
|---|---|---|---|
| 4,227,894 | 10/1980 | Proynoff | 361/231 |
| 4,649,935 | 3/1987 | Charmillot et al. | 128/783 |
| 4,911,737 | 3/1990 | Yehl et al. | 361/231 X |
| 5,197,941 | 3/1993 | Whitaker | 600/27 |

OTHER PUBLICATIONS

Chicago Tribune Article "Feeling Sour and Sluggish?" Nov. 10, 1991 2 pages.
"Air Ions: Physical and Biological Aspects" CRC Press 1987 Chapter 6 pp. 91–149, Charry et al.

Primary Examiner—Angela D. Sykes
Assistant Examiner—Samuel Gilbert

[57] ABSTRACT

A method for treating atypical depressive disorders characterized by reverse Neurovegetative symptoms such as hypersomnia, hyperphagia (with carbohydrate cravings) and fatigue in which a subject is exposed to high density negative ions produced by a high output negative ion generator at a density greater than $5.0 \times 10^5$ ions/cm$^2$ for brief periods of about 30 minutes per day for 10–20 successive days with the ions being supplied by a generator positioned close to the subject.

13 Claims, 2 Drawing Sheets

TREATMENT METHOD FOR DEPRESSIVE AND NEUROVEGETATIVE DISORDERS

BACKGROUND OF THE INVENTION

Clinical depression is marked prominently by symptoms of dysphoric mood often accompanied by anxiety, decreased interest in normal activities, work productivity, social interactions, and—in the extreme—a sense that life is not worth living, even leading to suicidal ideation and behavior. Depending on the depressive subtype, distinct sets of neurovegetative symptoms are apparent. "Classical" (melancholic) depressive disorders are marked by insomnia, reduced appetite and weight loss, and agitated behavior. By contrast, "atypical" depressive disorders—which are the present focus—are marked by continual fatigue, increased need for sleep (often with difficulty awakening), and increased appetite (often for carbohydrate-rich foods) and weight gain.

According to the official diagnostic classification of the American Psychiatric Association, disorders relevant to this application include Major Depressive Disorder (MDD, in which normal mood, or euthymia, is present outside the depressive episodes), Bipolar Disorders (in which mania or hypomania is sometimes present outside the depressive episodes), and "Not Otherwise Specified" disorders (NOS, in which depressive symptoms are clinically significant but do not meet severity criteria for MDD). Secondarily, these disorders may be further described as showing melancholic or atypical features, and as occurring in a seasonal pattern. These secondary descriptions do not define separate disorders, but rather clusters of specific symptoms and temporal course of clinical presentation.

Furthermore, clinical observation clearly shows individuals with neurovegetative disorders (of fatigability, hypersomnia and hyperphagia) that exist without depressed mood and yet are responsive to treatment interventions which are specifically active in atypical depressive disorders. Indeed, it has been noted that the onset of atypical depressive disorders can be initially detected in the emergence of the neurovegetative symptoms, with appearance of depressed mood occurring at a later stage.

It is now well acknowledged that the incidence of certain depressive disorders is not spontaneous or random, but is reliably triggered by external environmental factors. In one model, depressive disorders with seasonal pattern [which are also referred to outside the official diagnostic classification scheme as seasonal affective disorders (SAD)] are triggered by decreased environmental light exposure as the natural photoperiod contracts in autumn at northerly latitudes (winter depression) or, alternatively, by high temperature and humidity in summer (summer depression, in which a classical depressive profile is expressed). Atypical neurovegetative symptoms are hallmarks of winter depression; likewise, non-depressed individuals may show reliable cycles of wintertime fatigue, hypersomnia and hyperphagia (even including binge eating and bulimia nervosa, the latter being a diagnostically distinct eating disorder within the classification scheme of the American Psychiatric Association).

Although a majority of patients with winter depression regain normal levels of mood, energy, sleep and appetite in spring and summer, a distinct minority—estimated at one third of cases—becomes hypomanic, with exaggeratedly elevated (or "euphoric") mood and energy, often with racing thoughts, rapid speech and difficulty with concentration. Furthermore, the neurovegetative symptoms of winter are seen in the opposite extreme, with lower-than-normal appetite and greatly reduced sleep duration without loss of daytime energy.

Although, by formal definition, depressive disorders with seasonal pattern are characterized by normal mood, hypomania or mania outside the depressive episode, a large number of patients with chronic depressive disorders show wintertime exacerbation of symptoms as a seasonal overlay. Furthermore, a relatively small number of patients show both winter and summer depressive cycles, and are asymptomatic in fall and spring. Furthermore, many patients who meet criteria for seasonal pattern (winter type), show distinct slumps in mood and transient appearance of neurovegetative symptoms—short of meeting diagnostic criteria for severity and/or duration—during periods of bad weather during their normally asymptomatic seasons of the year.

In another variation, a similar clinical picture as found in winter depression may appear chronically, or intermittently but without seasonal pattern, given indoor environmental factors typical of the wintertime living and working environment. In one example, clinical observation shows that night shift workers, darkroom workers, and individuals who spend significant time in home or institutional environments with poor lighting are vulnerable to a light deprivation syndrome whose presentation is similar to that of winter depression. In another example, day workers at deficiently illuminated and ventilated work sites are vulnerable to a "sick building syndrome", which is characterized by atypical depressive symptoms above and beyond respiratory and digestive ailments presumably related to airborne pathogens.

It is estimated that about 10 million Americans suffer from winter depression at a fully syndromal level, with another 25 million suffering at a milder subsyndromal level which is less debilitating and may not meet diagnostic severity criteria. Prevalence estimates for nonseasonal atypical neurovegetative disorders are not yet known, but are thought to exceed that of disorders with seasonal pattern. Winter depression has been treated effectively with bright light therapy since it was first identified in the early 1980's, though the mechanism of action of light is still not well understood. The positive treatment effect, however, provides prima facie evidence that reduced daylight availability in fall and winter is a likely precipitant of the depressive episode. Indeed, the larger contraction of the natural photoperiod at more northerly latitudes is correlated with an increased prevalence of winter depression. Furthermore, patients with winter depression may show a sudden switch to hypomania shortly after initiation of light therapy, equal to or even exceeding the intensity of their summer episodes, in a light-dose-dependent manner. It is suspected that winter depression may also respond selectively to serotonergic antidepressants, although controlled trials are still largely lacking. Specific serotonin reuptake inhibitors are also known to serve as appetite suppressants. Therefore, it would be hypothesized that light itself activates serotonergic mechanisms.

BRIEF DESCRIPTION OF THE INVENTION

In accordance with the invention a method of treatment of humans demonstrating depressive and neurovegetative disorders has been discovered in which patients are treated with negative ions at a high density.

In accordance with the invention, human patient subjects determined to be affected with depressive disorders with seasonal pattern, winter type, are treated by placing them in an environment of high-density negative ions produced by an ion generator for at least one interval of time on a daily basis over a time period. In the preferred treatment mode, patients are treated by receiving 30 minutes of high density negative ion exposure upon awakening in the morning. The high density exposure was accomplished by placing an ion generator unit in proximity to the patient's head and with the ion-emitting electrodes pointing toward the patient. The treatment was carried out over a period of 10–20 days.

In a control procedure, negative ion exposure was adjusted to a low density ($1 \times 10^4$ ions/cm$^3$) and parallel treatment was administered to a separate group of patients, or to individual patients in different phases of a controlled study. A dose-dependent effect, in the absence of a directly detectable difference in negative ion concentration, provided evidence for the efficacy of the high-density negative ion treatment.

Clinical evaluation performed in accordance with accepted psychiatric evaluation techniques determined that there was a clinical remission of depressive and neurovegetative symptoms in a statistically significant number of patients. Although subjects were selected who showed symptoms with a seasonal pattern of recurrence, their primary diagnostic classifications (major depressive disorder, bipolar disorder, and the NOS variants) are shared by patients who do not show a seasonal pattern. Furthermore, an overlapping neurovegetative symptom pattern is shown by individuals suffering chronic fatigue syndrome, certain eating and weight control disorders, certain sleeping disorders, certain night shift work disturbances (including fatigability and carbohydrate cravings), and dysphoric reactions to environments with a predominance of positively charged air ions, and transient depressive reactions during periods of bad weather regardless of the season.

OBJECTS OF THE INVENTION

It is therefore an object of the present invention to provide a method for treating depressive and neurovegetative disorders, including those with seasonal pattern, by subjecting a patient to an exposure of high density negative air ions.

A further object is to provide a method of treating certain depressive and neurovegetative disorders in which a patient exhibiting symptoms of the syndrome is exposed to negative ions of relatively high density for a predetermined time period each day over a course of treatment time.

Another object is to provide a method for the treatment of patients determined to have certain depressive and neurovegetative disorders, including those with seasonal pattern, by exposing such patients to high density negative ions for a time period each day over the course of several weeks.

An additional object is to treat a patient to relieve the symptoms of certain depressive and neurovegetative disorders by subjecting the patient to an environment of negative ions at a relatively high density for a period of time each morning preferably upon the patient waking.

An further object is to provide a method for treating seasonal affective disorder (SAD) by exposing a patient to negative ions at a high density level.

BRIEF DESCRIPTION OF THE DRAWINGS

Other objects and advantages of the present invention will become more apparent upon reference to the following specification and annexed drawings in which.

DETAILED DESCRIPTION OF THE INVENTION

Figure 1:
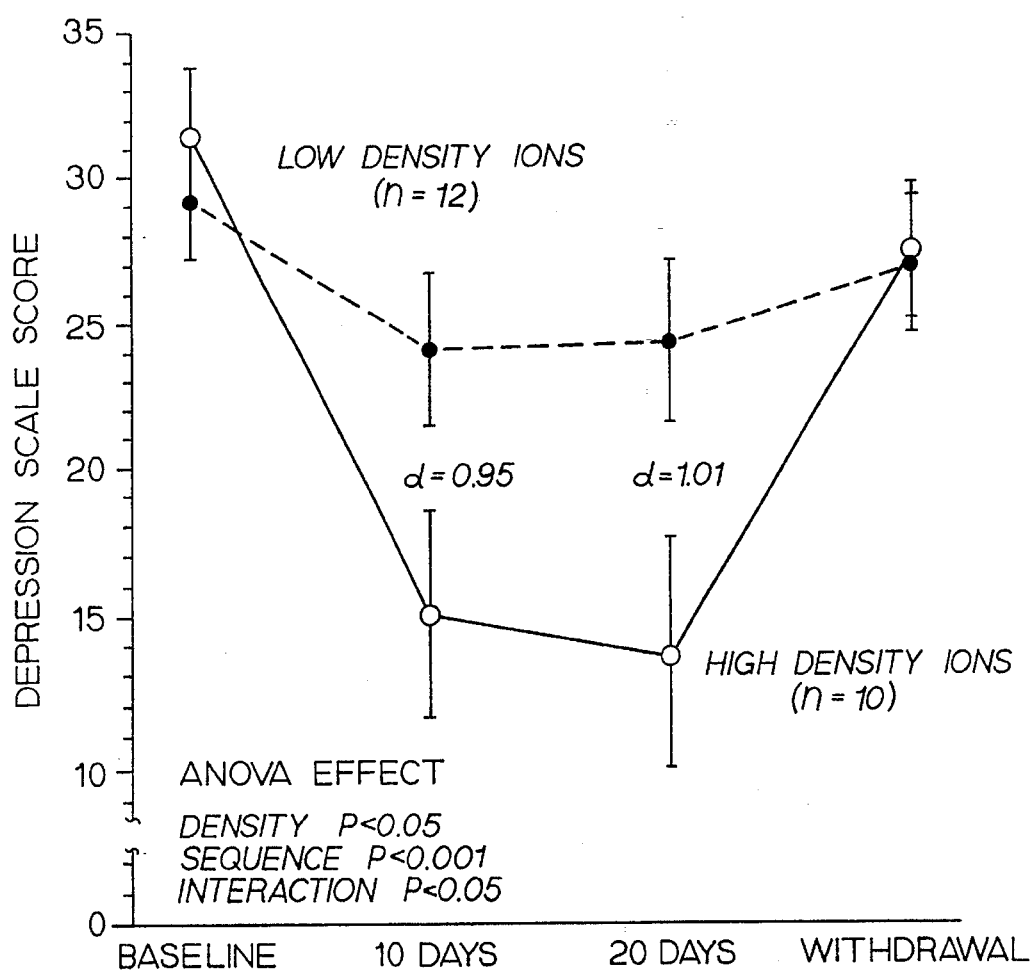
FIG. 1 shows depression-related scale scores for a group of patients.

In accordance with the invention a main protocol was established to select patients exhibiting depressive disorders with seasonal pattern (winter type), and the patients were treated using controls to demonstrate the efficacy of the treatment.

The main protocol had the following elements:

I. Recruitment

Media announcements were made of a sponsored clinical trial for patients possibly exhibiting depressive disorders with seasonal pattern (winter type) who would be treated with bright light and negative ion therapy. The announcement stated that there was no charge to the potential subjects and no compensation was to be paid.

II. Screening

Each applicant completed a preliminary application form which took an outline of the symptoms, history of symptoms, pattern and other medical conditions.

Telephone screening of each of the applicants discussed, reviewed and clarified the preliminary application and the applicant was given a description of the study and its procedures and a discussion of the willingness to comply with the study regimen.

If an applicant satisfied the telephone screening, an extended application was taken, this being an expansion of the preliminary application.

For the patients selected from the extended applications a clinical diagnostic evaluation took place during which each patient was subjected to a DSM-III-R interview (DSM being the standard diagnostic protocol of The American Psychiatric Association) and there was a review of the extended application.

A physical examination was conducted for each of the patients who satisfied the criteria of the evaluation (at the expense of the patient) including standard blood work and EKG (at no expense to the patient).

III. Intake Criteria

The criteria to be a subject qualifying for the study were:

Males and females, ages 18–65. No glaucoma, cataract or retinal disease and no potentially interactive medical condition. The evaluation included a structured interview DSM-III-R that focussed primarily on diagnosis of mood, anxiety, eating, and psychotic disorders. Diagnostic inclusion criteria included DSM-III-R 296.3 (which defines major depression which is recurrent), DSM-III-R 296.5 (bipolar disorder, depressed), DSM-III-R 296.70 (bipolar disorder NOS), or DSM-III-R 311.00 (depressive disorder NOS). All subjects selected for the study met criteria for DSM-III-R seasonal pattern, winter type. No other Axis I diagnosis or Axis II personality disorder was present. All patients showed a history of at least three recurrent winter depressive episodes, with normal mood or hypomania in spring and summer.

No use of psychotropic medication was permitted throughout the study period. No use of alcohol or recreational drugs was permitted throughout the study period.

IV. Baseline Evaluation

A baseline evaluation was made for each subject selected for the study on the following basis.

Clinical depression current meeting entry severity criteria (depression scale scores, Hamilton ≧10, atypical symptoms ≧5, total ≧20). The Hamilton scale is the established instrument for quantifying severity of classical depressive symptoms. The supplementary atypical symptoms scale encompasses the neurovegetative symptoms commonly (but not necessarily) seen in depressive disorders with seasonal pattern (winter type), as well as in nonseasonal atypical depressive disorders and certain neurovegetative disorders (such as eating and weight control syndromes) which are not necessarily accompanied by depressed mood per se. For entry into treatment, a second evaluation after two weeks was made to verify persistence of symptoms.

V. Randomization into Treatment Conditions

The subjects were randomly assigned for treatment either by high density negative ions, low density negative ions or light treatment. Patients were told that the treatment duration was to be approximately 20 days depression scale interviews were conducted by blind raters—that is, the raters did not know the treatment given to any subject, or whether the subject was in a treatment or withdrawal phase—at 10 and 20 day intervals. The criterion for a remission of depressive symptoms was a post-treatment reduction of the score≧50% relative to the baseline. Prior to initiation of treatment, all subjects signed an informed consent.

VI. Withdrawal from treatment

Treatment was to last for 20 days. A non-blind interviewer (who knew the treatment type for the subject) performed telephone monitoring of the clinical status of the subjects. Those subjects appearing to relapse were scheduled for prompt depression scale interviews (these were blind in that the interviewer of a relapsing subject did not know the treatment regimen for the subject). The other subjects were interviewed at 10–14 days. The criterion for a relapse was return to the baseline value or worse.

After the patients were selected they were divided in three groups for treatment. These were:

Group 1. Light therapy—the patients in this group were treated by 30 minute daily exposures to bright fluorescent light at 10,000 lux intensity, with the timing of treatment sessions exactly equivalent to that for patients who received the negative ions. The light treatment was used to present patients with an enlarged study scope so that their views would be focussed on the broader area of therapy for seasonal disorders, rather than just the use of negative ions.

For negative ion treatments (Groups 2 and 3 below), patients were treated with either "low" density or "high" density negative ions. These relative terms of "low" or "high" are selected in accordance with the definition in the volume *Air Ions: Physical and Biological Aspects*, CRC Press, 1987, p. 144), which describes various experiments with negative ions. In this publication, "low" density is defined as negative ions at $5.0\times10^3$ ions/cm$^3$, with "high" density being $5.0\times10^5$ ions/cm$^3$ and above. In this invention, the term "low" also includes the "medium" range defined in the publication, which is $2.0\times10^4$ ions/cm$^3$.

Group 2. High density negative ions—a "JoniCare" Model 45 negative ion generator made by Sea-King AB of Vasras Sweden was used. This generator is rated to produce an environment of $2\times10^6$ ions/cm$^3$ with an electron flow rate of $45\times10^{12}$/sec. Various factors, for example room size, openness of the area, etc., proximity of the generator to the patient, and generator output determine the time needed for the environment to achieve the desired ion density. A range of electron flow rates with which the invention is usable to produce the desired ion density is in the order of $16\times10^{12}$/sec to about $50\times10^{12}$/sec and preferably $45\times10^{12}$/sec. The generator was placed about three feet from the head of the patient with the ion producing electrodes pointing toward the patient's head. Closer placement—for example, at about 1.5 feet—also can be implemented so that more of the emitted negative ions reach the patient without picking up contaminants, such as by becoming attached to air molecules. When switched on for sessions, a red LED monitor light indicated operation of the unit. The time and duration of the exposure are given below.

Group 3. Low density negative ions—A "JoniCare" Model 45 negative ion generator was internally electrically modified to produce a lower concentration of negative ions, rated at $1\times10^4$ ions/cm$^3$. In all other respects its appearance and operation were identical to the high-density ion generator.

Patients exposed to negative ions were not informed as to whether they were receiving high density or low density negative ions. Patients exposed to both high and low density negative air ions were in a room at home with doors and windows closed, with any window air conditioner or fan turned off, and with room light not exceeding normal interior levels of about 300 lux. During treatments, patients sat on a chair facing the ion generator at a distance of about 3 feet, and engage in quiet activities such as reading, working, watching television, etc. The generator was placed on a tubular floor stand 38.5 in. above the floor, and was at least 3 feet from any adjacent wall surface. Items that might serve to dissipate ion density, such as telephone or telephone line, sink, radiator or other metal object, ventilation duct, and radio or other equipment, were out of proximity.

The results follow.

CONTROLLED STUDY OF HIGH- VS. LOW-DENSITY ION EXPOSURE IN 30-MINUTE MORNING SESSIONS

See main protocol description. Ten patients were randomized into high-density exposure, and 12 into low-density exposure, for a parallel-group comparison. High-density exposure was significantly more effective than low-density exposure, within 10 days of daily exposures lasting 30 minutes, and was persistent to 20 days of treatment at the same treatment level. (*): Scale score meets remission criterion of at least 50 per cent reduction relative to baseline.)

| SUBJECT | BASELINE | 10-DAY EVALUATION | 20-DAY EVALUATION | WITHDRAWAL |
| --- | --- | --- | --- | --- |
| High-density | | | | |
| 1 | 35 | 6* | 4* | 25 |
| 2 | 30 | 2* | 2* | 32 |
| 3 | 28 | 21 | 0* | 23 |
| 4 | 32 | 18 | 14* | 25 |
| 5 | 41 | 10* | 10* | 29 |

| SUBJECT | BASELINE | 10-DAY EVALUATION | 20-DAY EVALUATION | WITHDRAWAL |
|---|---|---|---|---|
| 6 | 20 | 12 | 26 | 20 |
| 7 | 27 | 6* | 11* | 30 |
| 8 | 38 | 13* | 7* | 23 |
| 9 | 41 | 35 | 34 | 44 |
| 10 | 22 | 28 | 29 | 25 |
| Low-density | | | | |
| 1 | 24 | 38 | 20 | 16 |
| 2 | 36 | 21 | 13* | 23 |
| 3 | 26 | 8* | 18 | 30 |
| 4 | 34 | 26 | 15* | 22 |
| 5 | 21 | 22 | 26 | 23 |
| 6 | 31 | 36 | 20 | 29 |
| 7 | 30 | 12* | 28 | 30 |
| 8 | 21 | 18 | 32 | 26 |
| 9 | 25 | 25 | 27 | 22 |
| 10 | 21 | 27 | 26 | 22 |
| 11 | 36 | 29 | 20 | 41 |
| 12 | 40 | 28 | 48 | 42 |

B. OVERNIGHT BEDROOM EXPOSURE TO HIGH-DENSITY IONS

In a follow-up procedure upon completion of the main protocol, 10 patients were given approximate 10-day trials of high-density negative ion exposure while in bed while sleeping. The ion generator was turned on at bedtime and turned off upon arising, for exposure durations of approximately 7–9 hours per night). The generator was placed approximately 3 feet from the pillow. Of these patients, half showed post-treatment depression scale scores that met the clinical remission criterion (*):

| SUBJECT | BASELINE | 10 DAY EVALUATION |
|---|---|---|
| 1 | 29 | 36 |
| 2 | 19 | 4* |
| 3 | 27 | 13* |
| 4 | 21 | 29 |
| 5 | 23 | 12* |
| 6 | 27 | 32 |
| 7 | 23 | 34 |
| 8 | 16 | 7* |
| 9 | 30 | 0* |
| 10 | 18 | 26 |

C. HIGH/LOW-DENSITY CROSSOVERS

In a follow-up procedure, three patients were given the ion density opposite to that they received in the original trial, i.e., those who had received high-density treatment were given placebo and those who has received placebo treatment were given high density. Of these, two showed selective response to high-density ions (*), and one showed response to both densities. Even so, the ostensible placebo responder showed a higher post-treatment score (increased symptomatology) following low-density exposure.

| SUBJECT | BASELINE | HIGH DENSITY | WITH-DRAWAL | LOW DENSITY |
|---|---|---|---|---|
| 1 | 28 | 0* | 23 | 26 |
| 2 | 21 | 3 | 25 | 8 |
| 3 | 30 | 0* | 30 | 32 |

SUMMARY OF DATA

As seen, the results of the high density negative ion treatment are positive. The high-density ion treatment is clearly statistically significantly superior to the low-density placebo control. Of a total of 18 patients within the controlled trial, 7/10 given high-density negative ion stimulation have shown clinical remissions, as measured by accepted psychiatric standards, by the end of two weeks of treatment, 5/10 within one week. By contrast, only two of the 12 placebo patients showed clinical remission. All patients who showed improvement under high-density treatment subsequently relapsed to near baseline levels within one week of withdrawal. Several subjects who responded well to high density negative ions reported in retrospect that they had presumed an assignment to the placebo condition and were surprised by the positive result.

Figure 2:
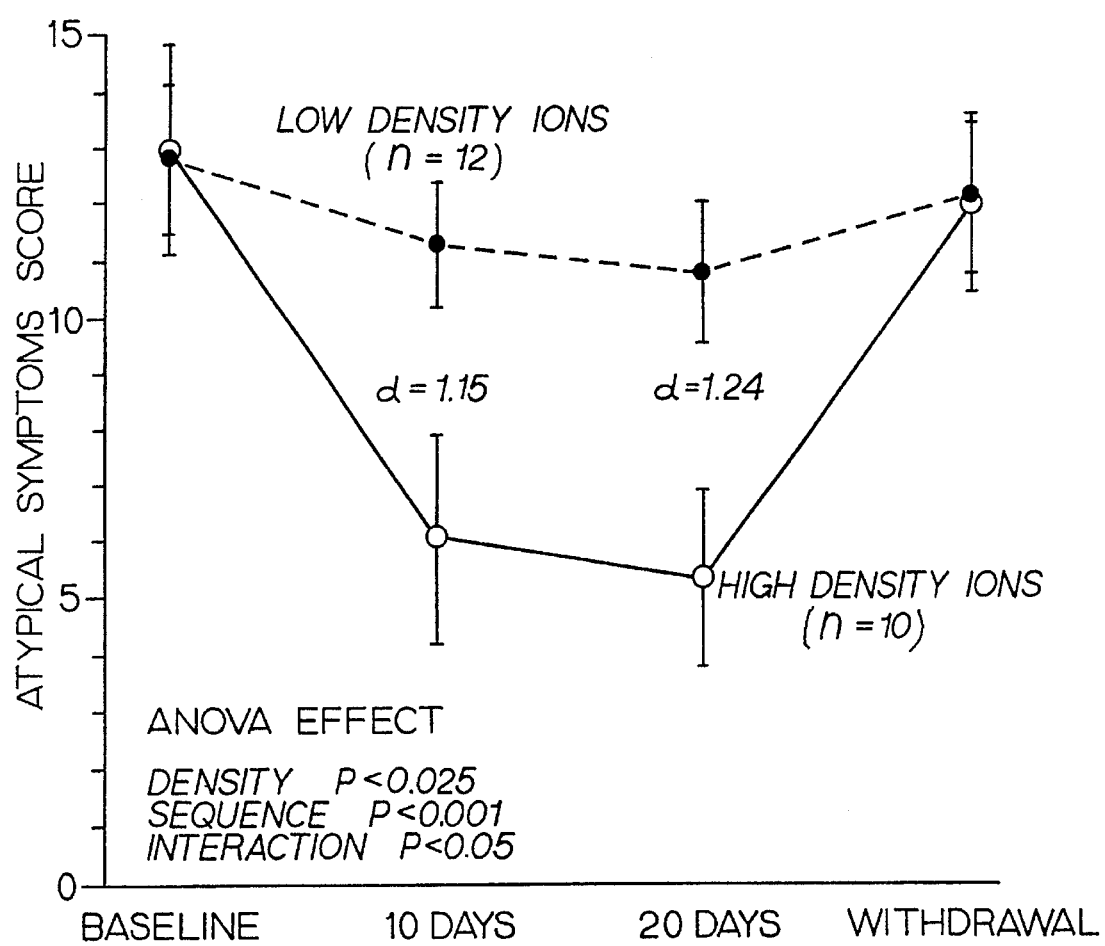
FIG. 2 shows scale scores that quantify the severity of atypical neurovegetative symptoms separately from depressed mood.

Graphical and statistical summaries of the controlled trial are presented in FIGS. 1 and 2, with assessment scale data expressed as mean ±SEM. As shown in FIG. 1, a two-way repeated measures analysis of variance on the total depression scale scores showed statistically significant effects of ion density, sequence of procedures, and their interaction. Subjects who received low density ions showed no significant change in scores under treatment. By contrast, those receiving high-density ions showed major improvement during the first 10 days of treatment, which was sustained at 20 days. The size of effect (d) was evaluated as the normalized difference between means. The size of effect between mean post-treatment scores at 10-day and 20-day treatment evaluations was large ($d=0.95$ and $1.01$, respectively, corresponding to reductions of about 15 scale points), and no significant between-group differences were found at baseline or withdrawal phases. Furthermore, baseline and withdrawal scores were closely matched and not significantly different.

The results for the scale of atypical symptom severity (exclusive of depressed mood) are shown separately in FIG. 2. A two-way repeated measures analysis of variance on the total scores showed statistically significant effects of ion density, sequence of procedures, and their interaction. Subjects who received low density ions showed no significant change in scores under treatment. By contrast, those receiving high-density ions showed major improvement during the first 10 days of treatment, which was sustained at 20 days. The size of effect between mean post-treatment scores at 10-day and 20-day treatment evaluations was large ($d=1.15$ and $1.24$, respectively, corresponding to reductions of about 6 scale points), and even exceeded those for the total depression scale, and no significant between-group differences were found at baseline or withdrawal phases. Furthermore, baseline and withdrawal scores were closely matched and not significantly different.

Such results compare favorably with antidepressant drug treatment studies. The time course of improvement is distinctly shorter than in most such studies, and more closely matches the rapid response seen under light therapy. The placebo response rate in the present studies (2/12 patients, or 17%, who received low density ions for 20 days) is similar to that of many controlled studies of antidepressant drugs or light (approximately 20%).

Two patients given high-density exposure became hypomanic within the first week of treatment, a pronounced side effect that sustains the conclusion of an active physiologic and antidepressant effect specific to high-density negative ion administration.

The results demonstrate an antidepressant effect of high-density negative air ions. Within the controlled study, 70 per cent of patients given high-density negative ions met the quantitative criterion for clinical remission (i.e., a reduction of post-treatment depression scale score of at least 50 per cent relative to baseline) within 20 days of treatment, whereas only 17 per cent of patients given low-density negative ions showed remission. By a hypothesis test of proportions, this contrast between active treatment and placebo is statistically significant ($\underline{P}<0.01$).

The results also indicate applicability to treatment of nonseasonal depressive syndromes as well as to seasonal syndromes that bear similarities to those characterized by depressive disorders, but without depressed mood per se (e.g., fatigue syndromes, weight control syndromes). Such syndromes are believed to involve underlying mechanisms common to those of depressive disorders with seasonal pattern (winter type).

I claim:

1. A method of achieving a therapeutic effect in a human subject experiencing at least one of depressive and neurovegetative symptoms comprising the steps of:

producing negative ions by an ion generator of a density of at least $5.0\times10^5$ ions/cm$^3$ to establish a high density negative ion environment sufficient to evoke a therapeutic response in which at least one of the frequency and severity of symptoms is clinically significantly reduced; and exposing the subject while in proximity to said ion generator to the environment of negative ions produced by said generator for about 30 minutes a day over a period of successive days sufficiently long to therapeutically effect the symptoms in a positive manner.

2. A method as in claim 1 wherein the exposing step comprises exposing the subject to said high density negative ion environment over a period of 10–20 days.

3. A method as in claim 2 wherein the producing step comprises producing the negative ions from said generator at a density greater than $5.0\times10^5$ ions/cm$^3$.

4. A method as in claim 1 wherein the step of producing negative ions by said ion generator comprises producing the negative ions at a density of $2.5\times10^6$ ions/cm$^3$.

5. A method as in claim 4 wherein the producing step includes producing the negative ions by said generator at an electron flow rate of about $1.6\times10^{12}$/sec to $50\times10^{12}$/sec.

6. A method as in claim 1 wherein said generator produces the negative ions at an electron flow rate of about $1.6\times10^{12}$/sec to $50\times10^{12}$/sec.

7. A method according to claim 6 wherein said generator produces the negative ions at an electron flow rate of $45\times10^{12}$/sec.

8. A method as in claim 1 further comprising exposing the subject to the negative ions upon awakening from overnight sleep.

9. A method as in claim 1 further comprising exposing the subject to the negative ions while the subject is sleeping.

10. A method as in claim 1 comprising treating a subject having depressive disorders with seasonal pattern.

11. A method as in claim 10 comprising treating a subject having seasonal affective disorder.

12. A method as in claim 1 wherein the exposing step comprises providing a unit which produces the negative ions and locating said unit within a distance of about 1.5 to about 3.0 feet of the subject.

13. A method as in claim 1 further comprising performing the exposing step in the morning.

* * * * *